(12) United States Patent
Bruder et al.

(10) Patent No.: US 7,711,081 B2
(45) Date of Patent: May 4, 2010

(54) METHOD FOR COMPILING COMPUTER TOMOGRAPHIC REPRESENTATIONS USING A CT SYSTEM WITH AT LEAST TWO ANGULARLY OFFSET RAY SOURCES

(75) Inventors: Herbert Bruder, Höchstadt (DE); Thomas Flohr, Uehlfeld (DE); Karl Schwarz, Roth (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 324 days.

(21) Appl. No.: 11/491,959

(22) Filed: Jul. 25, 2006

(65) Prior Publication Data
US 2007/0025499 A1 Feb. 1, 2007

(30) Foreign Application Priority Data
Jul. 26, 2005 (DE) .................... 10 2005 034 876

(51) Int. Cl.
*A61B 6/03* (2006.01)
(52) U.S. Cl. ................................. 378/9; 378/4
(58) Field of Classification Search .............. 378/4, 378/9, 15, 901
See application file for complete search history.

(56) References Cited

U.S. PATENT DOCUMENTS 4,891,829 A * 1/1990 Deckman et al. ............. 378/4
6,028,908 A * 2/2000 Taguchi ....................... 378/15

(Continued)

FOREIGN PATENT DOCUMENTS

DE 198 54 917 A1 6/2000

(Continued)

OTHER PUBLICATIONS

Kachelriess et al., Extended parallel backprojection for standard three-dimensional and phase-correlated four-dimensional axial and spiral cone-beam CT with arbitrary pitch, arbitrary cone-angle, and 100% dose usage, Jun. 2004, Medical Physics, vol. 31, No. 6, pp. 1623-1641.*

(Continued)

*Primary Examiner*—Chih-Cheng G Kao
*Assistant Examiner*—John M Corbett
(74) *Attorney, Agent, or Firm*—Harness, Dickey & Pierce, P.L.C.

(57) ABSTRACT

A method is disclosed for compiling computer tomographic representations using a CT system with at least two angularly offset ray sources. A first ray cone with a relatively larger fan angle and a second ray cone with a relatively smaller fan angle scan an object circularly or spirally. The first ray cone generates a first dataset A and the second ray cone generates a dataset B. The dataset B of the smaller ray cone is supplemented with other data at the edge to give an expanded dataset B+ for reconstruction of the CT representation. The expanded dataset B+ of the second, smaller ray cone and the dataset A of the first, larger ray cone is subjected to a convolution operation to give datasets B+' and A'. Finally, a back projection to reconstruct sectional images or volume data is respectively carried out from the convoluted datasets B+' and A'. The dataset B is supplemented with data of the dataset A and supplementary data are removed from the dataset B+' after the convolution but before the back projection.

20 Claims, 5 Drawing Sheets

U.S. PATENT DOCUMENTS

| | | | |
|---|---|---|---|
| 6,307,909 B1 | 10/2001 | Flohr et al. | |
| 6,819,736 B1* | 11/2004 | Bruder et al. | 378/15 |
| 6,839,400 B2* | 1/2005 | Bruder et al. | 378/4 |
| 2002/0015468 A1* | 2/2002 | Kohler et al. | 378/4 |
| 2002/0131549 A1* | 9/2002 | Oikawa | 378/19 |
| 2003/0076920 A1* | 4/2003 | Shinno et al. | 378/4 |
| 2004/0165695 A1* | 8/2004 | Karimi et al. | 378/19 |
| 2005/0111622 A1* | 5/2005 | Bruder et al. | 378/95 |
| 2005/0111623 A1* | 5/2005 | Bruder et al. | 378/95 |
| 2005/0175143 A1* | 8/2005 | Miyazaki et al. | 378/19 |
| 2006/0067458 A1* | 3/2006 | Chen | 378/4 |
| 2006/0104407 A1* | 5/2006 | Zamyatin et al. | 378/4 |

FOREIGN PATENT DOCUMENTS

| | | |
|---|---|---|
| WO | WO 2004/080310 A1 | 9/2004 |
| WO | WO 2004080310 A1 * | 9/2004 |

OTHER PUBLICATIONS

Taguchi et al., Algorithm for image reconstruction in multi-slice helical CT, Apr. 1998, Medical Physics, vol. 25, No. 4, pp. 550-561.*

Crawford et al., Computed Tomography Scanning with Simultaneous Patient Translation, 1990, Medical Physics, vol. 17, No. 6, pp. 967-982.*

Kak et al., Principles of Computerized Tomographic Imaging, 1988, IEEE Press, ISBN 0-87942-198-3.*

Hsieh, Computed Tomography: Principles, designs, artifacts, and recent advances, 2003, SPIE Press, ISBN 0-8194-4425-1, pp. 358-363.*

Kachelriess et al., Phase-Correlated Imaging from Multi-Threaded Spiral Cone-Beam CT Scans of the Heart, Jul. 7, 2005, The Eighth International Meeting on Fully Three-dimensional Image Reconstruction in Radiology and Nuclear Medicine, pp. 159-162.*

Bruder et al., Single-Slice Rebinning Reconstruction in Spiral Cone-Beam Computed Tomography, IEEE, Sep. 2000, vol. 19, No. 9, pp. 873-887.*

Sourbelle, Katia, Performance Evaluation of Exact and Approximate Cone-beam Algorithms in Spiral Computed Tomography, Mar. 25, 2002, Erlangen University, Dissertation, pp. 33-37.*

Kachelriess et al., Extended Parallel Backprojection (EPBP) for Arbitrary Cone Angle and Arbitrary Pitch 3D and Phase-Correlated 4D CT Reconstruction, 2003, Proceedings of the VIIth International Conference on Fully 3D Reconstruction in Radiology and Nuclear Medicine, pp. 1-5.*

K.Stierstorfer et al.: "Weighted FBP—a simple approximate 3D FBP algorithm for multislice spiral CT with good dose usage for arbitrary pitch", in: Physics in Medicine and Biology, vol. 49, 2004, pp. 2209-2218.

J.Hsieh et al.: "A novel reconstruction algorithm to extend the CT scan field-of-view", In: Medical Physics, vol. 31, No. 9, Sep. 2004, pp. 2385-2391.

* cited by examiner

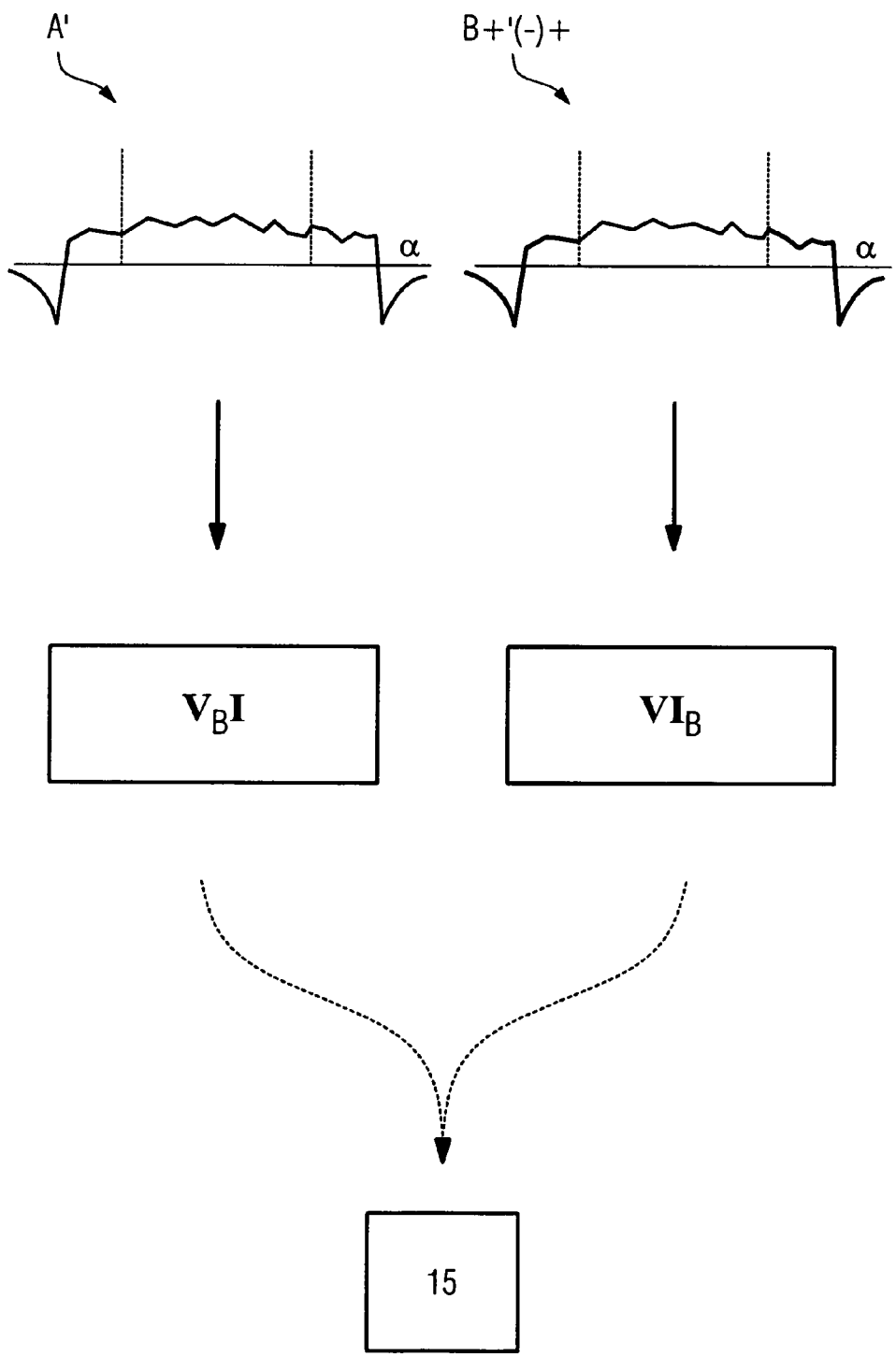

METHOD FOR COMPILING COMPUTER TOMOGRAPHIC REPRESENTATIONS USING A CT SYSTEM WITH AT LEAST TWO ANGULARLY OFFSET RAY SOURCES

PRIORITY STATEMENT

The present application hereby claims priority under 35 U.S.C. §119 on German patent application number DE 10 2005 034 876.9 filed Jul. 26, 2005, the entire contents of which is hereby incorporated herein by reference.

FIELD

The invention generally relates to a method for compiling computer tomographic representations. For example it may relate to one using a CT system with at least two angularly offset ray sources, wherein at least a first ray cone with a larger fan angle and a second ray cone with a smaller fan angle scan an object circularly or spirally and the first ray cone generates a first dataset A because of its absorption in the object and the second ray cone generates a dataset B, the B data of the smaller ray cone being supplemented with other data at the edge to give an expanded dataset B+ for reconstruction of the CT representation, the expanded B+ data of the first ray cone and the A data of the larger ray cone is subjected to a convolution operation to give B+' and A' data, and a back projection being carried out from the convoluted B+' and A' data.

BACKGROUND

To compile computer tomographic representations using a CT with a plurality of angularly offset ray sources, it is generally known to combine data from the individual ray sources and thereby carry out the reconstruction, i.e. a convolution of the data with subsequent back projection, for 2D or 3D reconstruction.

For reconstruction from a dataset of a ray cone which does not fully scan the object, it is furthermore known to supplement the peripherally existing sharp boundaries with corresponding extrapolations of data in order to reduce artifacts which have been created by a sharp delimitation of the data. In this regard, reference is made for example to document DE 198 54 917 A1 which describes such an extrapolation of peripheral data, albeit in a CT with a single-tube/single-detector system.

It has been found that both a simple data supplement in a CT system with a plurality of ray cones, respectively from the other ray cone, can lead to artifacts in the reconstruction of computer tomographic representations.

SUMMARY

A method is provided which, in at least one embodiment, allows a data supplement between ray cones in a CT with a plurality of offset ray cones but reduces or even avoids the artifacts occurring in the prior art.

In at least one embodiment, the inventors have discovered that it can be advantageous for the reconstruction to carry out the employed convolution with datasets which are respectively supplemented with data of another ray cone, but that the supplementary data should at least partially be removed again after the convolution and before the actual back projection.

In particular, such data removal is advantageous whenever the supplementary data come from complementary data of the other respective ray cone since, with these data, the filter direction which is normally carried out in the scan direction is incorrect for these complementary rays.

According to this basic concept, in at least one embodiment the inventors propose a method for compiling computer tomographic representations using a CT system with at least two angularly offset ray sources, wherein at least a first ray cone with a larger fan angle and a second ray cone with a smaller fan angle scan an object circularly or spirally and the first ray cone generates a first dataset A because of its absorption in the object and the second ray cone generates a dataset B, the B data of the smaller ray cone being supplemented with other data at the edge to give an expanded dataset B+ for reconstruction of the CT representation, the expanded B+ data of the first ray cone and the A data of the larger ray cone is subjected to a convolution operation to give B+' and A' data, and a back projection being carried out from the convoluted B+' and A' data, wherein the dataset B is supplemented with data of the dataset A and supplementary data are removed from the dataset B+' after the convolution but before the back projection.

This type of data supplement and subsequent data reduction reduces artifacts otherwise occurring in the CT representation.

In principle, either only data of the dataset A with the same ray direction may be used for supplementing the dataset B or data with the same ray direction and with a complementary ray direction may also be used. In respect of the data to be removed again after the convolution and before the back projection, on the one hand all the supplementary data may be removed from the dataset B+', or alternatively only the supplementary which come from complementary rays of the dataset A may be removed from the dataset B+'.

The reconstruction carried out may be a voxel-wise 3D reconstruction, or a planar 2D reconstruction may be carried out, in which case the data removed from the dataset B+' must be replaced by data from the convoluted dataset A' for the 2D reconstruction.

A different inclination of the rays relative to the z axis may furthermore be neglected when supplementing the dataset B with data of the dataset A. It is likewise possible to use interpolated data from the dataset A for supplementing the dataset B.

It is furthermore possible for weighting to achieve a smooth transition to be carried out in the supplemented dataset B+ at the transition between the data of the dataset B and the supplementary data from the dataset A.

According to at least one embodiment of the invention, different procedures may then be carried out with the result of the convolution of the original datasets A and B, either by recombining these datasets to give a common dataset before the back projection or by carrying out one back projection per dataset and generating the common image with this result.

In the latter case, a back projection may respectively be carried out separately with the dataset A' and with the dataset B+'(−), optionally with a further data supplement, and a common image may be generated by weighting. Transitional weighting can in this case advantageously be carried out in the transition range of the measurement field of the smaller ray cone B.

Corresponding to the former case, a common 2D back projection is thus carried out with the A' data and the—optionally postprocessed—B+'(−) data, to which end the two datasets may be combined by weighting to give a dataset A∪B before the back projections. Here, there is also the possibility of transitional weighting in the transition range of the data of the measurement field of the smaller ray cone B.

For the case of 3D reconstruction, a common 3D back projection may be carried out voxel-wise with the A' data and the—optionally postprocessed—B+'(−) data, and the two datasets may be combined by weighting to give a new dataset before the voxel-wise back projections.

According to at least one embodiment of the method described above, the Inventors also propose to improve a computer tomography system known per se for the tomographic representation of an object with at least two angularly offset ray sources, which form a first ray cone with a larger fan angle and a second ray cone with a smaller fan angle, scan an object circularly or spirally and generate detector output data, the first ray cone generating a first dataset A because of its absorption in the object and the second ray cone generating a dataset B, which are processed with the aid of stored computer programs or program modules in a computation and control unit to give tomographic representations of the object, so that the stored computer programs or program modules also comprise program code which implements the method steps described above.

BRIEF DESCRIPTION OF THE DRAWINGS

The invention will be explained in more detail below with reference to the example embodiments with the aid of the figures, only the features necessary for understanding the example embodiments of the invention being represented, the following reference numerals being used in the figures: 1: CT system with two X-ray tubes; 2: first tube; 3: first detector; 4: second tube; 5: second detector; 6: CT housing; 7: opening in the CT system; 8: displaceable patient support; 9: system axis, 10: control and computation unit; 11: large ray cone of the A system; 12: large measurement field of the A system; 13: small ray cone of the B system; 14: small measurement field of the B system; 15: image; A: data of the A system; B: data of the B system; $D_A$ detector of the A system; $D_B$ detector of the B system; $F_A$ focus of the A system; $F_B$ focus of the B system; P: patient; $Prg_1$-$Prg_n$: computer programs; α: projection angle; $β_A$: fan angle of the A system; $β_B$: fan angle of the B system; I-VI: method steps.

In detail:

FIG. 5 shows a variant with combination of the convoluted datasets of the two ray cones and back projection from the common dataset thus obtained to give a result.

DETAILED DESCRIPTION OF THE EXAMPLE EMBODIMENTS

Figure 1:
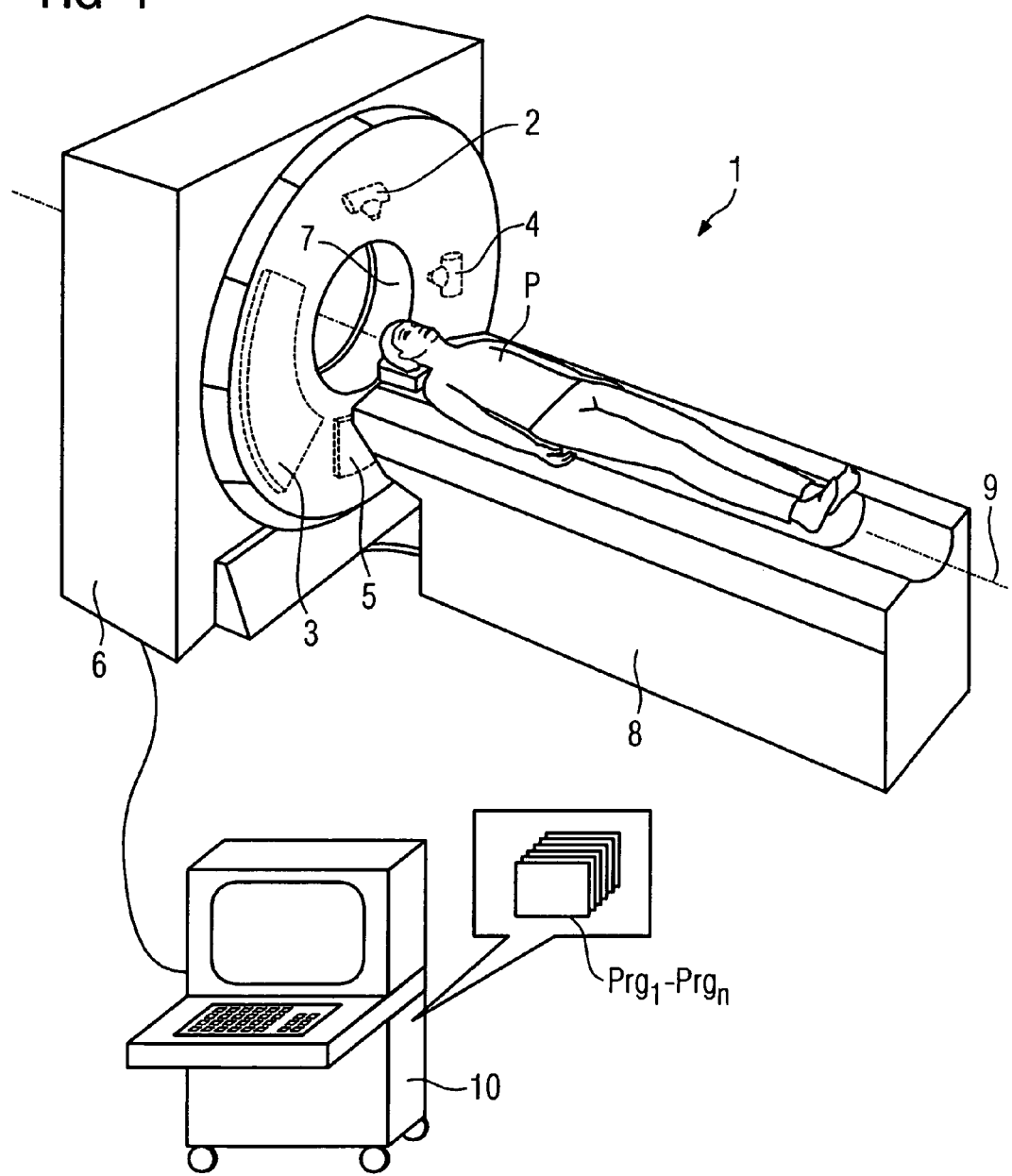
FIG. 1 shows a 3D view of a CT with two-tube-detector combinations.

FIG. 1 shows by way of example a computer tomographic system 1 having two tube/detector combinations supported on a gantry. The computer tomographic system 1 consists of a CT housing 6 which contains the two X-ray tubes 2 and 4, opposite which the detectors 3 and 5 are arranged, the tube/detector combinations 2, 3 having a smaller ray cone than the tube/detector combinations 4, 5.

A patient P, who can be moved along the system axis 9 through an opening 7 at the centre of rotation of the tube/detector combination, lies on a displaceable patient support 8, the actual scanning taking place either sequentially and circularly or, with a continuous forward movement of the patient, in a spiral-shaped profile relative to the patient.

The computer tomographic system 1 is controlled by a control and computation unit 10, in which the computer programs $Prg_1$ to $Prg_n$ employed to carry out the method are stored and can be used in operation.

Figure 2:
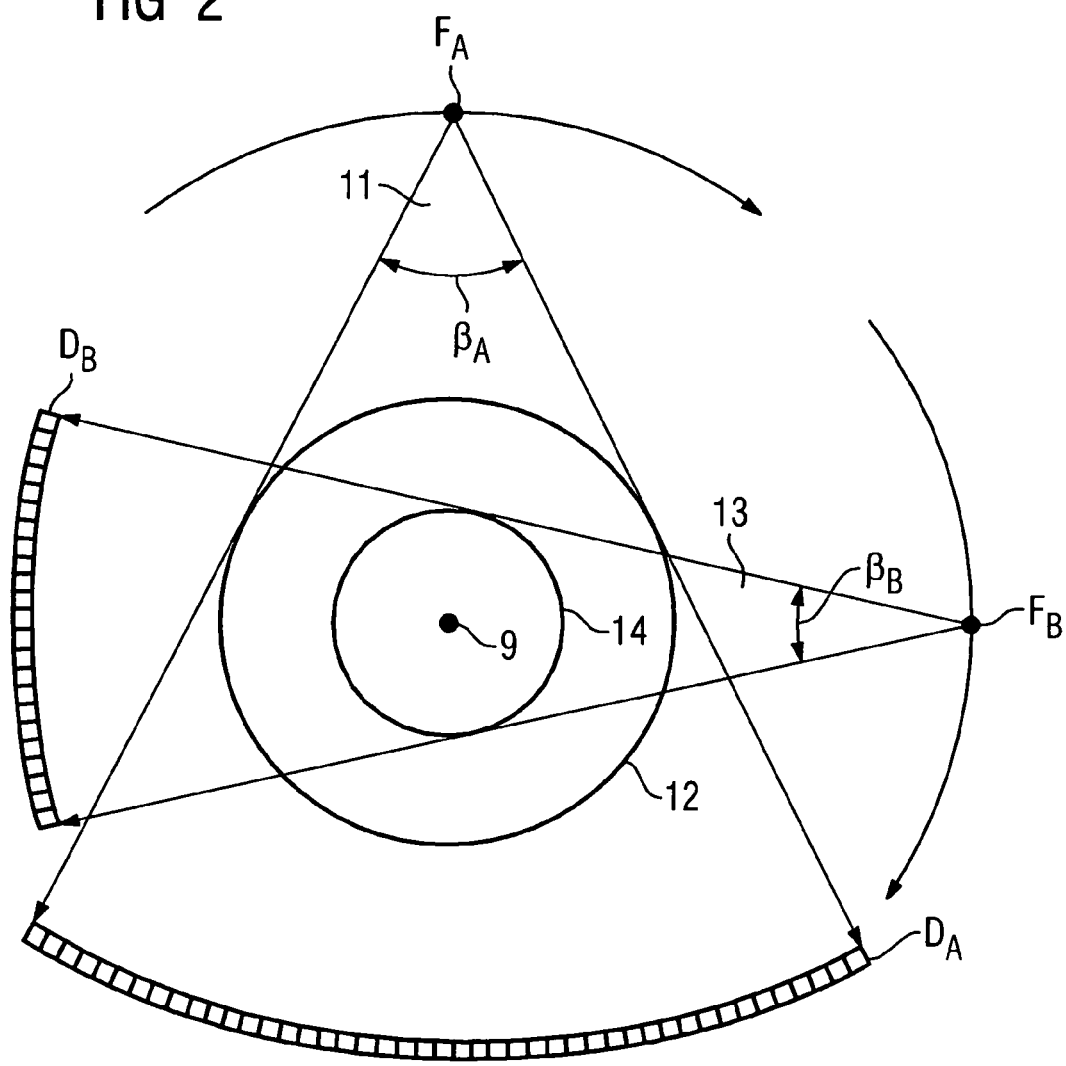
FIG. 2 shows a schematic sectional representation through a gantry of a two-tube-detector system.

A section through the gantry of such a system of FIG. 1 is represented in FIG. 2. This figure shows a first tube/detector system with a focus $F_A$, which forms a first ray cone 11 that strikes the detector $D_A$ arranged opposite and scans a measurement field 12 at the centre of rotation by its rotation in the circumferential direction. A second tube/detector system with a focus $F_B$, which has the same centre of rotation because it is fastened on the same gantry, is arranged offset by approximately 90°. The focus $F_B$ forms a ray cone 13 which strikes the detector $D_B$ arranged opposite and scans a measurement field 14 owing to its rotation.

The first ray cone 11 has a fan angle $β_A$ which is designed to be substantially greater than the fan angle $β_B$ of the second ray cone 13. The measurement field 12 associated with the focus $F_A$ is correspondingly much larger than the measurement field 14 of the focus $F_B$.

If objects which exceed the smaller measurement field 14 of the B system are studied with such a CT, then strong edge effects occur when convoluting the data of the B system for the reconstruction because the attenuation at the edge has not decreased to zero, but instead forms a sharp edge. As already mentioned above, a data supplement must in any case be carried out before the convolution. In the case according to the invention, this data supplement is carried out with data which come from the other ray cone 11, i.e. the A system.

Here, for each missing ray of the B detector, it is possible to look for a ray of the A detector so that, on the one hand, the direction of the ray coincides or so that a complementary ray then with the correct direction is used and, on the other hand, the z position of the rays must coincide as well as possible with the z positions of the rays from the B detector. Since the z position for an inclined ray is not the same over the entire ray length, the z position of the rays at a point where their distance from the z axis is least may for example be used for comparison here.

The different inclination of the rays relative to the z axis may be neglected in this method, although it should in any case be pointed out that the data supplement in the method presented here is in principle carried out approximately. Thus, the data used may be correspondingly interpolated if there are no exact supplementary rays.

In order to avoid hard transitions between the two data ranges, i.e. the original data range and the supplementary data range, it may be expedient to use weighting with the aid of a smooth transition function, for example a cosine function.

In principle, it is possible to apply the method according to at least one embodiment of the invention both to 2D reconstructions and to 3D reconstructions, in the case of a 2D reconstruction it being necessary for the data removed after the convolution to be replaced again, while in 3D reconstruction it is also possible to carry out the reformatting without supplementary data since compensation is provided here via the normalization which takes place anyway.

Figure 3:
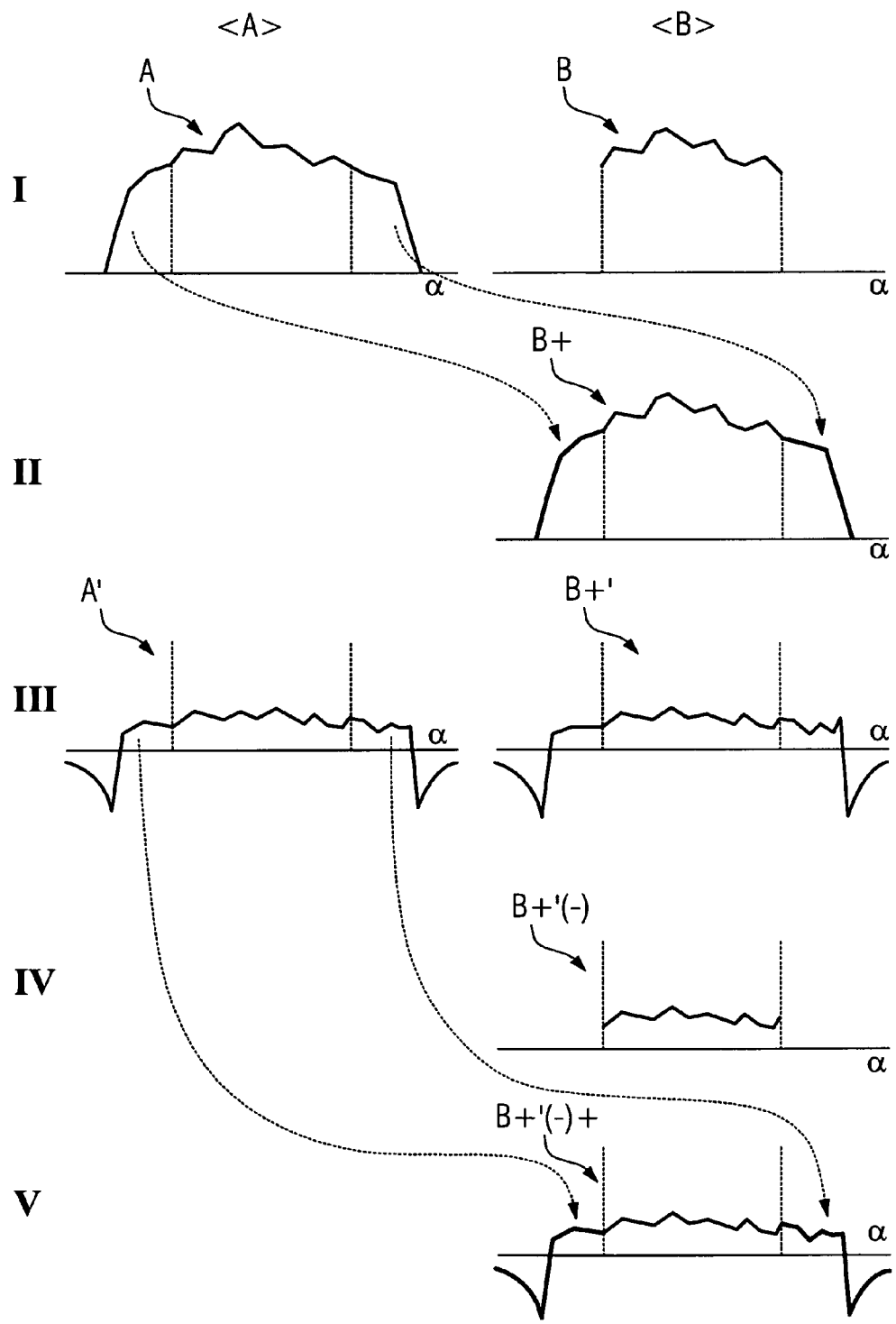
FIG. 3 shows a schematic representation of the combination of the datasets of two ray cones for a 2D reconstruction.

FIG. 3 again represents the method according to an embodiment of the invention schematically. FIG. 3 shows in columns <A> and <B> the datasets of a projection which come respectively from the A system and from the B system, the B system corresponding to the focus/detector combination with the smaller ray cone. The available data A and B of a projection taken by way of example are represented in row I, the projection angles α being plotted in the direction of the abscissa and the ordinate values corresponding to the attenuation values of the respective projection angle.

Owing to the smaller measurement field in column <B>, originally there are in fact only restricted data B there between the dotted lines which show the limits of the B system. In the first step, the data B not present in the B system are replaced by data A of the A system—represented by the two arrows between columns—and the dataset B+ is formed. A convolution is subsequently carried out for both sides, the result of which is represented by the datasets A' and B+' in row III. If the data lying outside the actual measurement field of the B system are now used for the back projection, then the resulting CT image would comprise increased artifacts—as already explained above. It is therefore more favorable for the convoluted data lying outside the B range now to be cut out again, so as to give the data B+'(−) represented in row IV. According to at least one embodiment of the invention, the already convoluted data A' of the A system can now be used in the range outside the B system in order thereby to supplement the data B+'(−), so as to give the dataset B+'(−)+, of row V which, for example, may be used for back projection in the 2D reconstruction.

Since both the convoluted dataset A' from the detector data of the further detector $D_A$, i.e. of the more widely fanned ray cone 11, and of the convoluted and supplemented dataset B+'(−) are now available, it is possible to proceed with the back projection in different ways.

Figure 4:
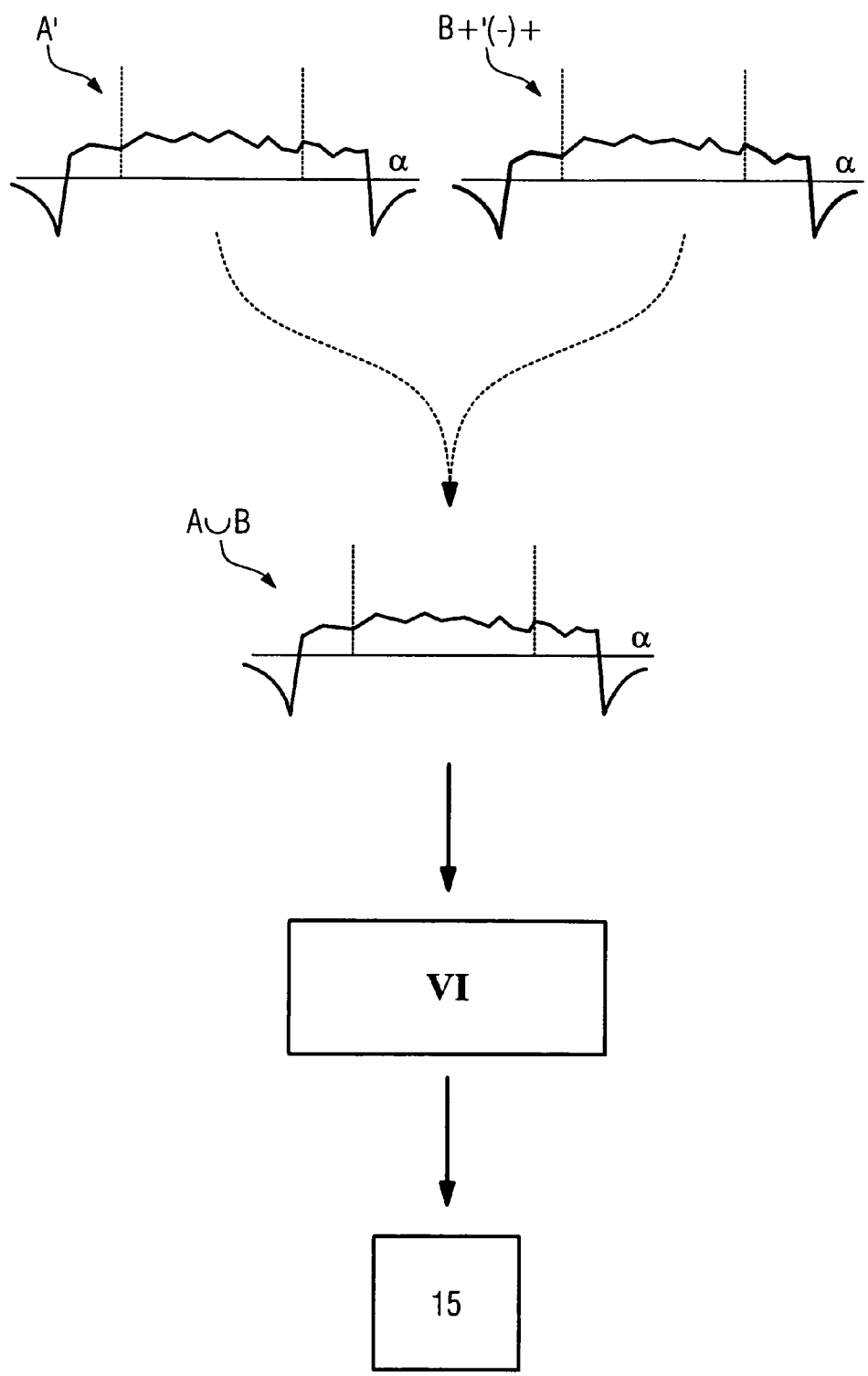
FIG. 4 shows a variant of the parallel back projection with datasets from the smaller and larger cones with subsequent combination of the results.

In one variant shown in FIG. 4, the two datasets A' and B+'(−)+ are combined for a 2D reconstruction. To this end simple averages or weighted averages may be formed in the range of the multiply present data, singly present data being adopted directly. It is also possible to carry out transitional weighting in the transition ranges. The resulting dataset A∪B can now be projected back in the next step VI so as to calculate the image 15.

Another variant of a 2D reconstruction according to at least one embodiment of the invention is shown in FIG. 5. Here, the two datasets A' and B+'(−)+ are projected back in separate steps $VI_A$ and $VI_B$ and only then combined to give a common image 15. The individual image values are averaged or weighted during the combination, and here again transitional weighting may be carried out in the transition regions.

A procedure similar to that described here for 2D reconstruction can also be applied to voxel-wise 3D reconstruction. This method according to at least one embodiment of the invention may be used in both reconstruction methods, which are based on a scan with at least two ray cones having different fan widths and scan fields of different sizes.

It is to be understood that the features of the embodiments of the invention as mentioned above may be used not only in the respectively indicated combination, but also in other combinations or individually, without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for compiling computer tomographic (CT) representations using a CT system with at least two angularly offset ray sources, the method comprising:

scanning an object circularly or spirally using a first ray cone, the first ray cone being a first ray source of the at least two angularly offset ray sources with a relatively larger fan angle and a second ray cone, the second ray cone being a second ray source of the at least two angularly offset ray sources with a relatively smaller fan angle;

generating, via the first ray cone, a first dataset A because of its absorption in the object and generating, via the second ray cone, a dataset B;

supplementing the dataset B of the smaller ray cone with other data at an edge to produce an expanded dataset B+ for reconstruction of the CT representation;

subjecting the expanded dataset B+ of the second, smaller ray cone and the dataset A of the first, larger ray cone to a convolution operation to produce datasets B+' and A'; and respectively carrying out a back projection to reconstruct at least one of sectional images and volume data from the convoluted datasets B+' and A', wherein the dataset B is supplemented with data of the dataset A, wherein supplementary data are removed from the dataset B+' after the convolution, but before the back projection to produce dataset B+'(−), and wherein the dataset B+'(−) is supplemented with convoluted dataset A' for the back projection.

2. The method as claimed in claim 1, wherein only data of the dataset A with the same ray direction are used for supplementing the dataset B.

3. The method as claimed in claim 1, wherein data of the dataset A with the same ray direction and with a complementarily directed ray direction are used for supplementing the dataset B.

4. The method as claimed in claim 1, wherein all the supplementary data are removed from the dataset B+'.

5. The method as claimed in claim 1, wherein only the supplementary data which come from complementary rays of the dataset A are removed from the dataset B+'.

6. The method as claimed in claim 1, wherein a voxel-wise 3D reconstruction is carried out.

7. The method as claimed in claim 1, wherein a planar 2D reconstruction is carried out and the data removed from the dataset B+' are replaced by data from the convoluted dataset A'.

8. The method as claimed in claim 1, wherein a different inclination of the rays relative to the z axis is neglected when supplementing the dataset B.

9. The method as claimed in claim 1, wherein interpolated data from the dataset A are used for supplementing the dataset B.

10. The method as claimed in claim 1, wherein weighting, to achieve a smooth transition, is carried out in the supplemented dataset B+ at the transition between the data of the dataset B and the supplementary data from the dataset A.

11. The method as claimed in claim 10, wherein a back projection is respectively carried out separately with the dataset A' and with a dataset B+'(−), optionally with a further data supplement, and a common image is generated by weighting, and
wherein the dataset B+'(−) represents the resulting data when supplementary data is removed from the dataset B+' after the convolution, but before the back projection.

12. The method as claimed in claim 11, wherein transitional weighting is carried out in the transition range of the measurement field of the smaller ray cone.

13. The method as claimed in claim 1, wherein a common 2D back projection is carried out with the A' data and the optionally postprocessed B+'(−) dataset.

14. The method as claimed in claim 13, wherein the two datasets are combined by weighting to give a dataset A'B+'(−) before the back projections.

15. The method as claimed in claim 13, wherein transitional weighting is carried out in the transition range of the data of the measurement field of the smaller ray cone.

16. The method as claimed in claim 1, wherein a common 3D back projection is carried out voxel-wise with the A' data and the optionally postprocessed B+'(−) dataset.

17. The method as claimed in claim 16, wherein the two datasets are combined by weighting to give a dataset A∪B before the back projections.

18. A computer tomography system for the tomographic representation of an object, comprising:
at least two angularly offset ray sources, forming a first ray cone with a relatively larger fan angle and a second ray cone with a relatively smaller fan angle, to scan an object circularly or spirally and generate detector output data, the first ray cone to generate a first dataset A because of its absorption in the object and the second ray cone to generate a dataset B; and
means for processing the data sets to produce tomographic representations of the object, the means for processing performing the steps of claim 1.

19. A computer readable medium including at least one of programs and program modules for, when executed on a computer, causing the computer to implement the method of claim 1.

20. A computer tomography (CT) system for the tomographic representation of an object, comprising:
at least two angularly offset ray sources, forming a first ray cone with a relatively larger fan angle and a second ray cone with a relatively smaller fan angle, to scan an object circularly or spirally and generate detector output data, the first ray cone to generate a first dataset A because of its absorption in the object and the second ray cone to generate a dataset B; and
a processor configured to process the data sets and to produce tomographic representations of the object by performing the steps of,
scanning the object circularly or spirally using the first ray cone with a relatively larger fan angle and the second ray cone with a relatively smaller fan angle;
generating, via the first ray cone, a first dataset A and generating, via the second ray cone, a dataset B;
supplementing the dataset B of the smaller ray cone with other data at an edge to produce an expanded dataset B+ for reconstruction of the CT representation;
subjecting the expanded dataset B+ of the second, smaller ray cone and the dataset A of the first, larger ray cone to a convolution operation to produce datasets B+' and A'; and
respectively carrying out a back projection to reconstruct at least one of sectional images and volume data from the convoluted datasets B+' and A', wherein the dataset B is supplemented with data of the dataset A, wherein supplementary data are removed from the dataset B+' after the convolution, but before the back projection to produce dataset B+'(−), and wherein the dataset B+'(−) is supplemented with convoluted dataset A' for the back projection.

* * * * *